(12) United States Patent
Nakano et al.

(10) Patent No.: US 10,327,445 B2
(45) Date of Patent: *Jun. 25, 2019

(54) ANTIVIRAL MATERIAL, ANTIVIRAL FILM, ANTIVIRAL FIBER, AND ANTIVIRAL PRODUCT

(71) Applicants: KABUSHIKI KAISHA TOSHIBA, Tokyo (JP); TOSHIBA MATERIALS CO., LTD., Yokohama-shi, Kanagawa (JP)

(72) Inventors: Kayo Nakano, Yokohama (JP); Akira Sato, Yokohama (JP); Takao Kusaka, Yokohama (JP); Shinya Kasamatsu, Yokohama (JP); Akito Sasaki, Yokohama (JP); Daisuke Fukushi, Yokohama (JP)

(73) Assignees: KABUSHIKI KAISHA TOSHIBA, Tokyo (JP); TOSHIBA MATERIALS CO., LTD., Yokohama-Shi (JP)

( * ) Notice: Subject to any disclaimer, the term of this patent is extended or adjusted under 35 U.S.C. 154(b) by 149 days.

This patent is subject to a terminal disclaimer.

(21) Appl. No.: 14/261,982

(22) Filed: Apr. 25, 2014

(65) Prior Publication Data

US 2014/0234385 A1 Aug. 21, 2014

Related U.S. Application Data

(63) Continuation of application No. 13/369,722, filed on Feb. 9, 2012, now Pat. No. 8,741,349, which is a continuation of application No. PCT/JP2010/005052, filed on Aug. 12, 2010.

(30) Foreign Application Priority Data

Aug. 12, 2009 (JP) .................................. 2009-187560

(51) Int. Cl.
| | | |
|---|---|---|
| *A61K 33/24* | (2019.01) |
| *B01J 23/30* | (2006.01) |
| *B01J 35/00* | (2006.01) |
| *B01J 35/02* | (2006.01) |
| *B01J 35/10* | (2006.01) |
| *B01J 37/34* | (2006.01) |
| *B01J 23/652* | (2006.01) |
| *B01J 23/888* | (2006.01) |
| *A01N 25/12* | (2006.01) |
| *A01N 59/16* | (2006.01) |
| *A61K 33/38* | (2006.01) |
| *B01J 23/34* | (2006.01) |
| *B01J 37/02* | (2006.01) |
| *B01J 37/04* | (2006.01) |
| *B01J 35/06* | (2006.01) |
| *C03C 17/00* | (2006.01) |
| *B01J 21/06* | (2006.01) |

(52) U.S. Cl.
CPC ............. *A01N 25/12* (2013.01); *A01N 59/16* (2013.01); *A61K 33/24* (2013.01); *A61K 33/38* (2013.01); *B01J 23/30* (2013.01); *B01J 23/34* (2013.01); *B01J 23/6527* (2013.01); *B01J 23/888* (2013.01); *B01J 35/002* (2013.01); *B01J 35/004* (2013.01); *B01J 35/023* (2013.01); *B01J 35/06* (2013.01); *B01J 35/1009* (2013.01); *B01J 35/1014* (2013.01); *B01J 35/1019* (2013.01); *B01J 35/1023* (2013.01); *B01J 37/0201* (2013.01); *B01J 37/0215* (2013.01); *B01J 37/04* (2013.01); *B01J 37/349* (2013.01); *C03C 17/006* (2013.01); *B01J 21/063* (2013.01); *B01J 21/066* (2013.01); *C03C 2217/42* (2013.01); *C03C 2217/70* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 3,920,578 A | * | 11/1975 | Yates ....................... B01J 20/28 |
| | | | | 106/287.1 |
| 4,740,246 A | * | 4/1988 | Feagin ...................... B22C 1/00 |
| | | | | 106/38.22 |
| 5,629,922 A | * | 5/1997 | Moodera ................ B82Y 25/00 |
| | | | | 257/421 |
| 6,362,121 B1 | | 3/2002 | Chopin et al. |
| 8,173,573 B2 | * | 5/2012 | Nakano ..................... A61L 9/18 |
| | | | | 502/305 |
| 8,404,617 B2 | * | 3/2013 | Nakano ..................... A61L 9/16 |
| | | | | 502/305 |
| 8,741,349 B2 | * | 6/2014 | Nakano .................. A61K 33/24 |
| | | | | 424/404 |

(Continued)

FOREIGN PATENT DOCUMENTS

| | | |
|---|---|---|
| JP | 10-033921 A | 2/1998 |
| JP | 2000-041667 A | 2/2000 |

(Continued)

OTHER PUBLICATIONS

United States Court of Appeals for the Federal Circuit. *Magsil Corporation v. Hitachi Storage Technologies Inc.* Case No. 2011-1221. Decided Aug. 14, 2012. pp. 1-14.*

(Continued)

*Primary Examiner* — Isaac Shomer
(74) *Attorney, Agent, or Firm* — Foley & Lardner LLP

(57) ABSTRACT

In one embodiment, an antiviral material includes at least one microparticles selected from tungsten oxide microparticles and tungsten oxide composite microparticles. The microparticles have an inactivation effect R of 1 or more expressed by [R=log C−log A], when there is evaluated a virus titer by inoculating on a specimen to which the microparticles are adhered, at least one virus selected from a low pathogenic avian influenza virus (H9N2), a high pathogenic avian influenza virus (H5N1) and a swine influenza virus, and irradiating the specimen with visible light having a wavelength of 380 nm or more and illuminance of 6000 lx. for 24 hours.

13 Claims, No Drawings

(56) References Cited

U.S. PATENT DOCUMENTS

| | | |
|---|---|---|
| 2004/0202723 A1 | 10/2004 | Yu et al. |
| 2005/0025700 A1* | 2/2005 | Bulian .................. B82Y 30/00 423/606 |
| 2005/0121110 A1* | 6/2005 | Dallam ................ B23K 35/362 148/23 |
| 2007/0187653 A1 | 8/2007 | Takeda et al. |
| 2008/0119352 A1 | 5/2008 | Kitaguchi |
| 2008/0308775 A1 | 12/2008 | Yabuki |
| 2009/0023583 A1* | 1/2009 | Nakano .................... A61L 9/16 502/309 |
| 2010/0040655 A1 | 2/2010 | Ren et al. |
| 2010/0113254 A1 | 5/2010 | Sato et al. |
| 2010/0204040 A1 | 8/2010 | Nakano et al. |
| 2010/0204041 A1 | 8/2010 | Nakano et al. |
| 2011/0052662 A1* | 3/2011 | Nakano .................. A61L 2/232 424/443 |

FOREIGN PATENT DOCUMENTS

| | | |
|---|---|---|
| JP | 2005-144383 A | 6/2005 |
| JP | 2006-198464 A | 8/2006 |
| JP | 2008-106342 A | 5/2008 |
| JP | 2009-119189 A | 6/2009 |
| JP | WO 2009110233 A1 * | 9/2009 ............. A61L 2/232 |
| WO | WO-2006/049025 A1 | 5/2006 |
| WO | WO-2007/023558 A1 | 3/2007 |
| WO | WO 2007/093808 A2 | 8/2007 |
| WO | WO-2008/117655 A1 | 10/2008 |
| WO | WO 2009/022100 A1 | 2/2009 |
| WO | WO 2009/031316 A1 | 3/2009 |
| WO | WO 2009/031317 A1 | 8/2009 |
| WO | WO 2009/096177 A1 | 8/2009 |
| WO | WO 2010/032445 A1 | 3/2010 |

OTHER PUBLICATIONS

Kazuhito Hashimoto et al., "Possibility of Photocatalyst Technology", Clean Technology, vol. 19, No. 6, Jun. 2009, pp. 1-5.

Hirofumi Togeda et al., "Development and Applied Evolution of Photocatalyst Technology", Syntehsiology, vol. 1, No. 4, 2008, pp. 287-295.

JIS R 1702, "Fine ceramics (advanced ceramics, advanced technical ceramics)—Test method for antibacterial activity of photocatalytic products under photoirradiation and efficacy", Japanese Industrial Standard, 2006.

JIS Z 9112, "Classification of Flourescent Lamps by Chromaticity and Colour Rendering Property", Japanese Industrial Standard, 1990.

Tadashi Kawai et al., "Experiments on Concrete Corrosion Protection Effect of Antibacterial Concrete", vol. 42, No. 507, Jan. 2005, pp. 163-174.

Translation of International Preliminary Report on Patentability of PCT/JP2010/005052, dated Mar. 22, 2012, 6 pages.

S. Supothina et al., "Synthesis of tungsten oxide nanoparticles by acid precipitation method", Ceramics International, vol. 33, 2007, pp. 931-936.

Certified English Translation of Foreign Priority document JP-2009-187560, filed Aug. 12, 2009, translation certified Mar. 22, 2017 by Etsuko Makino.

* cited by examiner

ANTIVIRAL MATERIAL, ANTIVIRAL FILM, ANTIVIRAL FIBER, AND ANTIVIRAL PRODUCT

CROSS-REFERENCE TO RELATED APPLICATION

This application is a continuation of U.S. application Ser. No. 13/369,722, filed Feb. 9, 2012, which is a continuation of prior International Application No. PCT/JP2010/005052, filed on Aug. 12, 2010 which is based upon and claims the benefit of priority from Japanese Patent Application No. 2009-187560 filed on Aug. 12, 2009; the entire contents of all of which are incorporated herein by reference.

FIELD

Embodiments described herein relate generally to an antiviral material, an antiviral film, an antiviral fiber, and an antiviral product.

BACKGROUND

In recent years, infection diseases caused by various viruses such as new type influenza viruses or bacteria such as 0157 threaten human life, so that a measure against the threat is urgently needed on a global basis. From such a point of view, a demand for antibacterial and antiviral materials increases, and antibacterial and antiviral properties are required for various products. Currently, application with respect to the antiviral property has advanced, but a material having sufficient performance with respect to the antiviral property has not been developed, yet.

A photocatalyst has a function of decomposing organic matters by light irradiation, and is a material in which antibacterial and antiviral effects are expected, and an antiviral product in which a titanium oxide-based photocatalyst is mixed, and the like have been put into practical use. However, the photocatalyst made of titanium oxide is excited only by ultraviolet rays, so that sufficient performance cannot be obtained in indoor environments having only a small amount of ultraviolet rays. Antiviral performance of a filter using titanium oxide is known. However, the antiviral performance uses ultraviolet rays contained in a fluorescent lamp, and cannot exhibit a sufficient effect under practical illuminance or in room space in which ultraviolet rays are cut by a shade or the like, resulting in that the performance is insufficient.

In order to improve visible light responsiveness of titanium oxide, visible light response-type photocatalysts based on titanium oxide carrying platinum compounds exhibiting performance even by visible light, titanium oxide doped with nitrogen or sulfur, and the like have been developed. However, the visible light response-type photocatalyst based on titanium oxide has a narrow excitation wavelength range, and thus sufficient performance has not been obtained under low illuminance of general interior lighting. With respect to the antiviral property as well, similarly, practical products have not been obtained under the present circumstances.

Products required for the antiviral property are touched by people, or used in an environment where people exist, and a product that exhibits antiviral performance regardless of in an outdoor environment or indoor environment is preferable. The photocatalyst material is one in which its performance is exhibited by light irradiation, and a material that exhibits antiviral performance regardless of a light irradiation amount of a usage environment is more preferable. It is said that viruses are inactivated by alcohol, but this is a temporary effect at the time when alcohol is applied to a product, and the product itself does not inactivate the viruses, and thus there is a possibility that viruses attach to the product again. Further, the effect varies also according to types of viruses. An Ag ion or the like is also said to be effective for the virus inactivation, but has a problem of low duration of the effect.

Tungsten oxide has a band gap narrower than that of titanium oxide, so that it receives attention as a material capable of obtaining photocatalysis by visible light. As for an antiviral function of tungsten oxide, it has been known that growth of sulfur oxidizing bacteria is inhibited under an environment of pH 2.5. Further, it has also been known that tungsten oxide is mixed with titanium oxide to obtain an antiviral property by photocatalysis. However, an antiviral material based on tungsten oxide has not been known. As described above, as for a conventional antiviral material, it has been difficult to evaluate an antiviral effect, so that a practical antiviral material has not been obtained so far. Development of an antiviral material having an antiviral effect regardless of an outdoor environment or indoor environment has been expected.

DETAILED DESCRIPTION

According to one embodiment, there is provided an antibacterial material including at least one microparticles selected from tungsten oxide microparticles and tungsten oxide composite microparticles. The microparticles, which are undergone a test to evaluate a virus titer by inoculating on a specimen, to which the microparticles are adhered in a range of not less than 0.01 mg/cm$^2$ nor more than 40 mg/cm$^2$, at least one virus selected from a low pathogenic avian influenza virus (H9N2), a high pathogenic avian influenza virus (H5N1) and a swine influenza virus, and irradiating with visible light having a wavelength of 380 nm or more and illuminance of 6000 lx for 24 hours by using a white fluorescent lamp and an ultraviolet cutting filter, by a method based on Test method for antibacterial activity of photocatalytic products under photoirradiation and efficacy of JIS-R-1702 (2006), have an inactivation effect R of 1 or more expressed by [R=log C−log A], where C denotes a virus titer TCID obtained after irradiating an unprocessed specimen with the visible light for 24 hours, and A denotes a virus titer TCID50 obtained after irradiating the specimen having the microparticles with the visible light for 24 hours.

Hereinafter, an antiviral material in an embodiment will be explained. The antiviral material according to the embodiment includes at least one microparticles selected from tungsten oxide microparticles and tungsten oxide composite microparticles, which will be referred to as tungsten oxide based microparticles hereinafter. The tungsten oxide based microparticles have an inactivation effect R of 1 or more, when the microparticles are adhered to a specimen to be subjected to an antiviral evaluation test. Further, the tungsten oxide based microparticles preferably have the inactivation effect R of 2 or more.

The test that evaluates antiviral performance is conducted by a method based on Test method for antibacterial activity of photocatalytic products under photoirradiation and efficacy of JIS-R-1702 (2006). As for the inactivation effect R, there are evaluated a virus titer A obtained after at least one virus selected from a low pathogenic avian influenza virus (H9N2), a high pathogenic avian influenza virus (H5N1), and a swine influenza virus is inoculated on a specimen to which the tungsten oxide based microparticles to be evaluated are adhered in a range of not less than 0.01 mg/cm² nor more than 40 mg/cm², and is irradiated with visible light having a wavelength of 380 nm or more and illuminance of 6000 lx for 24 hours by using a white fluorescent lamp and an ultraviolet cutting filter, and a virus titer C obtained after a similar virus is inoculated on an unprocessed specimen and is irradiated with visible light from a similar light source for 24 hours, and from these virus titers A and C, the inactivation effect R is obtained based on Expression (1) below.

$$R = \log C - \log A \quad (1)$$

The evaluation of the virus titers is conducted by a method described low. A virus is inoculated on a sample and is irradiated with light, and then a virus solution is diluted with a physiological saline solution to be collected, and is measured. The collected virus is diluted ten times and is allowed to infect cultured MDCK cells (Madin-Darby canine kidney cells) to be cultured for five days at 37° C. at a $CO_2$ concentration of 5%. After the culturing, the presence or absence of cell morphological transformation (a cytopathic effect) is observed and an amount of the virus that has infected the 50% cultured cell is calculated, and thereby a virus titer per 1 ml (TCID50/ml) is obtained.

In general, visible light corresponds to light whose wavelength is in a range of 380 nm 830 nm. In order to evaluate the performance under visible light irradiation, the evaluation in this embodiment is set that visible light having only a wavelength of 380 nm or more is used. Concretely, it is preferable to perform the evaluation by irradiation of visible light having only a wavelength of 380 nm or more by using a white fluorescent lamp defined in JIS-Z-9112 as a light source and an ultraviolet cutting filter cutting light whose wavelength is less than 380 nm. As the white fluorescent lamp, for example, FL20SS·W/18 made by Toshiba Lighting & Technology Corporation or an equivalent thereof is used. As the ultraviolet cutting filter, for example, Clarex N-169 made by Nitta Jushi Kogyo Co., Ltd., or an equivalent thereof is used.

When evaluating an antiviral property of the tungsten oxide based microparticles, first, a dispersion liquid is produced by mixing the microparticles (a fine powder) with a dispersion medium such as water and performing dispersion processing thereof by an ultrasonic dispersion machine, a wet jet mill, a beads mill, or the like. The obtained dispersion liquid is applied to a specimen such as a glass plate by a general method such as dropping, spin coating, dipping, spraying, or the like to produce a sample. A virus is inoculated on such a sample to evaluate the antiviral property. When the tungsten oxide based microparticles have photocatalytic performance, for exhibiting the photocatalytic performance in a state where the microparticles are applied to a surface of the specimen, it is preferable to set conditions not to give too much distortion to the powder in the dispersion processing.

The antiviral material including the tungsten oxide based microparticles includes not only just the tungsten oxide based microparticles but also materials produced by already-known methods such as a material having the microparticles applied to a base material, a material having the microparticles kneaded into a base material or a fiber, and a material having a surface layer containing the microparticles formed in a forming process of a base material. In the case when antiviral performance of such a material is evaluated, an evaluation test is conducted with a specimen cut out of the material. As a method of applying the microparticles to a base material, similarly to the antiviral property evaluation test of the microparticles, there is cited a method of using a dispersion liquid produced by performing dispersion processing on a mixture of the powder, a dispersion liquid, and a dispersing agent to be mixed according to need. In the case when uniformity of a film is required, as an application method, a method such as spin coating, dipping, spraying, or the like is preferably applied.

At least one microparticles selected from the tungsten oxide microparticles and the tungsten oxide composite microparticles are quite high in dispersibility, and thus a film exhibiting antiviral performance can be formed. In the case when conventional tungsten oxide microparticles having a large particle diameter are used, a film cannot be formed on a base material, and thus it is not possible to evaluate an antiviral property. Furthermore, in the case when conventional tungsten oxide microparticles having a large particle diameter are used, a film exhibiting antiviral performance is not obtained.

The tungsten oxide based microparticles used for the antiviral material in this embodiment have the inactivation effect R of 1 or more under conditions of 24-hour irradiation of visible light having illuminance of 6000 lx. That is, the tungsten oxide based microparticles exhibit good antiviral performance against at least one virus selected from a low pathogenic avian influenza virus (H9N2), a high pathogenic avian influenza virus (H5N1), and a swine influenza virus in the case when an amount of the microparticles adhering to the specimen is in a range of 0.01 to 40 mg/cm².

The antiviral performance of the tungsten oxide based microparticles is exhibited regardless of in an outdoor environment or indoor environment, and is further exhibited even in an indoor environment having relatively low illuminance. As above, the tungsten oxide based microparticles used for the antiviral material exhibit antiviral performance under irradiation of visible light. Thus, even in the case when the antiviral material including such tungsten oxide based microparticles is applied to a product to be used in an indoor environment having low illuminance such as an indoor ceiling, a wall, a floor, furniture, or a home electric appliance, practical antiviral performance can be obtained.

In the case when the tungsten oxide based microparticles used for the antiviral material are irradiated with visible light having illuminance of 6000 lx for 24 hours, the inactivation effect R is preferably 1 or more, and is more preferably 2 or more. Further, in the case when a visible light irradiation time is set to 4 hours, the inactivation effect R is preferably 0.5 or more. Further, in the case when they are irradiated with visible light having illuminance of 1000 lx for 24 hours, the inactivation effect R is more preferably 1 or more. By using the tungsten oxide based microparticles satisfying such conditions, a material having higher antiviral performance can be achieved. The material using such tungsten oxide based microparticles can exhibit high antiviral performance without being affected by illuminance of an environment.

The particle diameter of the tungsten oxide based microparticles is small and a photocatalytic activity thereof is high, and thus, the antiviral material according to this embodiment easily comes into contact with not only the influenza viruses but also various viruses such as a non-enveloped adenovirus and Norovirus and an enveloped herpes virus and SARS virus, and further decomposes proteins of viruses to thereby be able to inactivate the viruses.

The above-described antiviral material can be obtained by controlling the particle diameter (specific surface area), a crystal structure, and the like of the tungsten oxide based microparticles. The microparticles used for the antiviral material are not limited to the microparticles of tungsten oxide, and may also be microparticles of a tungsten oxide composite. The tungsten oxide composite is such that tungsten oxide as a main component contains a transition metal element or other metal elements. The transition metal element is an element with an atomic number from 21 to 29, 39 to 47, 57 to 79, or 89 to 109. The tungsten oxide composite preferably contains at least one metal element selected from T Zr, Mn, Fe, Pd, Pt, Cu, Ag, Zn, Al, and Ce. At least one type of metal element selected from Cu, Ag, and Zn is effective and a small amount of which can improve antiviral performance.

The content of the metal element such as the transition metal element in the tungsten oxide composite is preferably set to fall within a range of 0.01 to 50 mass %. When the content of the metal element exceeds 50 mass %, there is a risk that the property as the antiviral material deteriorates. The content of the metal element is more preferably 10 mass % or less, and is still more preferably 2 mass % or less. The lower limit value of the content of the metal element is not particularly limited, but the content thereof is preferably set to 0.01 mass % or more. The content of at least one metal element selected from Cu, Ag, and Zn is preferably set to fall within a range of 0.01 to 1 mass % in consideration of an effect that the tungsten oxide microparticles have and an effect of adding the metal element.

In the tungsten oxide composite used for the antiviral material, the metal element may exist in various forms. The tungsten oxide composite can contain a metal element in the form of a single metal element, a compound including a metal element (compound including oxide), a complex compound with tungsten oxide, or the like. The metal element contained in the tungsten oxide composite may itself form a compound with other elements. An example of a typical form of the metal element is oxide. The metal element is mixed with, for example, a tungsten oxide powder in the form of a single element, a compound, or a complex compound. The metal element may also be carried by the tungsten oxide.

As a concrete example of the tungsten oxide composite, there is cited a mixed powder that contains a copper oxide powder in a range of 0.01 to 5 mass %. Also a metal oxide powder (titanium oxide powder, iron oxide powder or the like) other than the copper oxide powder is preferably contained in the tungsten oxide composite in a range of 0.01 to 10 mass %. The tungsten oxide composite may also contain a tungsten compound other than the oxide, which is tungsten carbide. Tungsten carbide is preferably mixed, as its powder, with the tungsten oxide powder in a range of 0.01 to 5 mass %.

The method of combining the tungsten oxide with the metal element (concretely a single element, a compound, or a complex compound of at least one element selected from Ti, Zr, Mn, Fe, Pd, Pt, Cu, Ag, Zn, Al, and Ce) is not particularly limited, and various combining methods such as a mixing method to mix powders with each other, an impregnation method, a carrying method, and so on can be applied. A typical combining method is described below. As a method of combining copper with tungsten oxide, there is cited a method to mix tungsten oxide powder and copper oxide powder. Another effective method is such that the tungsten oxide powder is mixed in an aqueous solution or an ethanol solution of copper nitrate or copper sulfate, dried thereafter at a temperature of 70 to 80° C., and burned at temperatures of 500 to 550° C.

Further, it is also possible to apply a method to disperse the tungsten oxide powder in an aqueous copper chloride solution or an aqueous copper sulfate solution, and dry the above dispersion liquid (impregnation method). The impregnation method is not limited to a method of combining copper, and can be applied to a method of combining iron using an aqueous iron chloride solution, a method of combining silver using an aqueous silver chloride solution, a method of combining platinum using an aqueous platinum chloride solution, a method of combining palladium using an aqueous palladium chloride solution, and the like. Moreover, tungsten oxide may also be combined with a metal element (oxide) using an oxide sol such as a titanium oxide sol or an alumina sol. Besides them, various combining methods can be applied.

The tungsten oxide based microparticles used for the antiviral material preferably have a mean particle diameter (D50) in a range of 1 to 200 nm as a mean primary particle diameter. Further, the tungsten oxide based microparticles preferably have a BET specific surface area in a range of 4.1 to 820 $m^2/g$. The mean particle diameter is obtained based on a mean particle diameter (D50) of integrated diameters with reference to volumes of microparticles with n=50 or more from an image analysis of a picture such as SEM or TEM. The mean particle diameter (D50) may also match the mean particle diameter converted from the specific surface area.

When the microparticles have larger specific surface area and smaller particle diameter, the performance of the microparticles having the antiviral property is higher. When the mean primary particle diameter of the tungsten oxide based microparticles exceeds 200 nm or when the BET specific surface area is less than 4.1 $m^2/g$, it becomes difficult to form a uniform and stable film to cause a risk that sufficient antiviral performance cannot be obtained. When the mean primary particle diameter of the tungsten oxide based microparticles is less than 1 nm or when the BET specific surface area exceeds 820 $m^2/g$, the microparticles are too small, which provide poor handleability (handleability as a powder) and thus practicality of the antiviral material deteriorates. The BET specific surface area of the tungsten oxide based microparticles more preferably falls within a range of 8.2 to 410 $m^2/g$, and the mean primary particle diameter more preferably falls within a range of 2 to 100 nm.

The mean primary particle diameter of the tungsten oxide based microparticles more preferably falls within a range of 2.7 to 75 nm, and still more preferably falls within a range of 5.5 to 51 nm. The BET specific surface area preferably falls within a range of 11 to 300 $m^2/g$, and more preferably falls within a range of 16 to 150 $m^2/g$. When the tungsten oxide based microparticles are used for a coating material having an antiviral property or when they are kneaded into a base material and used, if the particle diameter of the microparticles is too small, the dispersibility of the microparticles decreases. For improving such a point, the tungsten oxide based microparticles having a mean primary particle diameter of 5.5 nm or more are preferably used.

The tungsten oxide based microparticles preferably contain 15% or more of microparticles having a primary particle diameter of 40 nm or less. The size of bacteria is 0.5 to 2 μm or so, but the size of viruses is 10 to 300 nm or so, which is small, and is $1/10$ to $1/100$ the size of bacteria. Thus, it is effect to make a large number of finer microparticles exist in the tungsten oxide based microparticles in order to inactivate viruses. Further, the tungsten oxide based microparticles preferably contain a large number of uniform and fine microparticles, but when the tungsten oxide based microparticles contain large microparticles but contain a large number of fine microparticles, an effect can be exhibited. When a large number of microparticles having a small particle diameter exist in the tungsten oxide based microparticles, high antiviral performance can be exhibited against a virus in a form having an envelope on its surface, in particular.

It is preferable that tungsten oxide which composes the tungsten oxide microparticles or the tungsten oxide composite microparticles has at least one crystal structure selected from a monoclinic crystal and a triclinic crystal of tungsten trioxide, or a crystal structure in which a rhombic crystal is mixed with at least one selected from the monoclinic crystal and the triclinic crystal. The tungsten oxide microparticles and the tungsten oxide composite microparticles using the tungsten oxide having such a crystal structure can stably exhibit excellent antiviral performance. Although it is difficult to determine abundance ratios of the respective crystal phases of tungsten trioxide, it can be estimated that tungsten oxide has the above-described crystal structure when it satisfies conditions (1) and (2) described below when measured by X-ray diffractometry.

(1) In an X-ray diffraction chart, a first peak (a diffraction peak with the highest intensity among all peaks), a second peak (a diffraction peak with the second highest intensity), and a third peak (a diffraction peak with the third highest intensity) exist in 2θ range from 22.5 to 25°.

(2) In the X-ray diffraction chart, an intensity ratio of a peak A to a peak D (A/D) and an intensity ratio of a peak B to the peak D (B/D) are in a range of 0.5 to 2.0, and an intensity ratio of a peak C to the peak D (C/D) is in a range of 0.04 to 2.5, where the peak A is a peak existing in 2θ range from 22.8 to 23.4°, the peak B is a peak existing in 2θ range from 23.4 to 23.8°, the peak C is a peak existing in 2θ range from 24.0 to 24.25°, and the peak D is a peak existing in 2θ range from 24.25 to 24.5°.

The measurement and analysis of the X-ray diffraction will be explained. In the measurement of the X-ray diffraction, it is set that a Cu target and a Ni filter are used, only smoothing and background subtraction are performed so as to prevent the analysis from being affected by a difference in processing condition, and peak intensities are measured without any Kα2 removal. Here, as for the way to read the peak intensities in the 2θ ranges in the X-ray diffraction chart, when a mountain is clearly seen, high positions of the mountain in the above range are considered as peaks and heights of the peaks are read. When a mountain is not clearly seen but there are shoulders, the shoulder portions are considered as peaks in the above range and heights of the shoulder portions are read. In the case of a gradient without any mountain or shoulder, heights at mid-points in the above range are read and the read values are considered as the peak intensities in the range.

When the crystallinity of the tungsten oxide based microparticles is low, or when the particle diameter of the tungsten oxide based microparticles is quite small, the tungsten oxide based microparticles are sometimes in one of cases (1) to (3) described below when measured by X-ray diffractometry. Such a case indicates that a large number of finer microparticles exist in the tungsten oxide based microparticles, and thus high antiviral performance can be obtained.

(1) In the X-ray diffraction chart, only a first peak exists in 2θ range from 22.5 to 25°, and a half value width of the peak is 1° or more.

(2) In the X-ray diffraction chart, the first and second peaks exist in 2θ range from 22.5 to 25°, and an intensity of a valley between the peaks is 10% or more of an intensity of the first peak.

(3) In the X-ray diffraction chart, the first, second, and third peaks exist in 2θ range from 22.5 to 25°, and an intensity of a lowest valley among valleys each between the peaks is 10% or more of an intensity of the first peak.

Further, in the X-ray diffraction chart of the tungsten oxide based microparticles, in the case when the first peak, the second peak, and the third peak exist in 2θ range from 22.5 to 25°, and the intensity of each of the valleys between the peaks is 10% or more of the intensity of the first peak, it is indicated that a large number of finer microparticles exist in the tungsten oxide based microparticles. Thus, by using the tungsten oxide based microparticles as above, high antiviral performance can be obtained.

By using the tungsten oxide based microparticles having the particle diameter (specific surface area) and the crystal structure as described above, the material exhibiting antiviral performance can be achieved. By applying such an antiviral material to a product to be used in an indoor environment having low illuminance such as an indoor ceiling, a wall, a floor, furniture, or a home electric appliance, practical antiviral performance can be obtained even under an environment having low illuminance.

Tungsten oxide has been known to have photocatalysis. The tungsten oxide based microparticles used for the antiviral material in this embodiment can exhibit high antiviral performance even under visible light irradiation having low light irradiation by satisfying the above-described particle diameter (specific surface area) and crystal structure, and further by increasing the crystallinity of the tungsten oxide or the tungsten oxide composite. For example, as for the above-described peak intensity ratio in the X-ray diffraction chart, when the intensity ratio of the peak A to the peak D (A/D) and the intensity ratio of the peak B to the peak D (B/D) each fall within a range of 0.7 to 2.0, and the intensity ratio of the peak C to the peak D (C/D) falls within a range of 0.5 to 2.5, the photocatalytic activity increases, and much better antiviral performance can be exhibited.

In the case of a titanium oxide-based photocatalyst, it is possible to improve visible light responsiveness by doping nitrogen or sulfur to then increase absorbing performance of visible light. Further, by controlling a heat treatment temperature to then improve crystallinity, or by carrying metal, it is possible to increase a photocatalytic activity by preventing re-combination of electrons and positive holes. However, in titanium oxide that exhibits high performance under significantly high illuminance, the performance deteriorates in accordance with the decrease in the illuminance. Titanium oxide that exhibits practical photocatalytic performance under low illuminance being a common level is not obtained.

By using the tungsten oxide based microparticles satisfying the conditions as described above, a material having higher antiviral performance in a general indoor environment can be obtained. The visible light with which the antiviral material is irradiated may also be not only light from the above-described white fluorescent lamp but also light from a general illumination, such as sunlight, a white LED, an electric bulb, a halogen lamp, or a xenon lamp, or a blue light emitting diode, a blue laser, or the like as a light source. Further, when the antiviral material is irradiated with light having high illuminance, higher antiviral performance can be exhibited thereby.

The reason why the antiviral material in this embodiment exhibits high antiviral performance is that by increasing the specific surface area of the tungsten oxide based microparticles, and by further containing a large number of finer microparticles in the tungsten oxide based microparticles, a contact area with viruses is increased, thereby allowing an active site to be increased, and additionally the crystallinity improvement decreases establishment of the re-combination of electrons and positive holes.

Tungsten oxide has a band gap of 2.5 to 2.8 eV, which is smaller than that of titanium oxide, and accordingly, it absorbs visible light. Thus, it is possible to achieve excellent visible light responsiveness. Further, a typical crystal structure of tungsten oxide is $ReO_3$ structure, so that a crystal plane having oxygen on an outermost layer of its surface and having a high reaction activity is likely to be exposed. For this reason, tungsten oxide exhibits a high hydrophilic property by absorbing water. Alternatively, an OH radical is produced by oxidizing the absorbed water, and thereby a molecule and a compound can be oxidized, so that it becomes possible that the photocatalytic performance that is better than that provided by an anatase or rutile crystal of titanium oxide is exhibited. Besides, the tungsten oxide based microparticles in this embodiment is excellent in dispersibility because its zeta potential in an aqueous solution with pH 1 to 7 is minus, and thus can be applied thinly and evenly on a base material.

The tungsten oxide based microparticles (powder) used for the antiviral material may also contain a metal element as impurities. The content of the metal element as an impurity element is preferably 2 mass % or less. Examples of the impurity metal element are an element normally contained in a tungsten mineral, a contaminant element that is mixed when a tungsten compound or the like used as a raw material is produced, and so on, and examples thereof are Fe, Mo, Mn, Cu, Ti, Al, Ca, Ni, Cr, Mg, and the like, for example. It is not limited to the above examples when these elements are used as constituent elements of a composite.

The tungsten oxide based microparticles (powder) used for the antiviral material in this embodiment are preferably produced by a method described below, but it is not limited thereto. The tungsten oxide microparticles are preferably produced by applying a sublimation process. Further, combining a heat treatment process with the sublimation process is also effective. With tungsten trioxide based microparticles produced by such a method, the above-described mean primary particle diameter, BET specific surface area, and crystal structure can be achieved stably. Moreover, the mean primary particle diameter approximates to the value converted from the BET specific surface area, and microparticles with small dispersion in particle diameter (fine powder) can be provided stably.

The sublimation process will be described. In the sublimation process, tungsten trioxide microparticles are obtained by sublimating a metal tungsten powder, a tungsten compound powder, or a tungsten compound solution in an oxygen atmosphere. The sublimation is a phenomenon that a state change from a solid phase to a vapor phase, or from a vapor phase to a solid phase occurs without undergoing a liquid phase. The tungsten oxide powder in a microparticle state can be obtained by oxidizing the metal tungsten powder, tungsten compound powder, or tungsten compound solution as a raw material while sublimating it.

Any one of the metal tungsten powder, tungsten compound powder, and the tungsten compound solution may be used as the raw material (tungsten material) in the sublimation process. Examples of the tungsten compound used as the raw material include tungsten trioxide ($WO_3$), tungsten dioxide ($WO_2$), tungsten oxide of a low-grade oxide or the like, tungsten carbide, ammonium tungstate, calcium tungstate, tungstic acid, and the like.

By performing the sublimation process of the tungsten raw material as described above in the oxygen atmosphere, the metal tungsten powder or the tungsten compound powder is turned from a solid phase to a vapor phase instantly, and further the metal tungsten vapor turned to a vapor phase is oxidized, to thereby obtain the tungsten oxide microparticles. Even when the solution is used, it turns to a vapor phase after being tungsten oxide or compound. Thus, the tungsten oxide microparticles can be obtained by using oxidation reaction in a vapor phase. Moreover, the crystal structure of the tungsten oxide microparticles can be controlled.

As the raw material for the sublimation process, at least one selected from a metal tungsten powder, a tungsten oxide powder, a tungsten carbide powder, and an ammonium tungstate powder is preferably used because the tungsten oxide microparticles obtained by sublimation in the oxygen atmosphere hardly contain impurities. The metal tungsten powder and the tungsten oxide powder are preferred particularly as raw materials for the sublimation process because they do not contain any harmful by-product (substance other than the tungsten oxide) formed in the sublimation process.

As the tungsten compound used for the raw material, a compound containing tungsten (W) and oxygen (O) as its constituent elements is preferred. Containing W and O as constituent elements makes it easy to be sublimated instantly when inductively-coupled plasma processing or the like described later is applied in the sublimation process. Examples of such a tungsten compound include $WO_3$, $W_{20}O_{58}$, $W_{18}O_{49}$, $WO_2$, and the like. Further, a solution, salt, or the like of tungstic acid, ammonium paratungstate, or ammonium metatungstate, is also effective.

When the tungsten oxide composite microparticles are produced, a transition metal element or other elements may also be mixed in the form of metal, compound including oxide, complex compound, or the like, in addition to the tungsten material. By processing the tungsten oxide with other elements simultaneously, complex compound microparticles of complex oxide of the tungsten oxide and other elements, or the like can be obtained. The tungsten oxide composite microparticles can also be obtained by mixing the tungsten oxide microparticles with or carrying them on single microparticles or compound microparticles of other metal elements. The method of combining the tungsten oxide with other metal elements is not particularly limited, and it is possible to apply various publicly known methods.

The metal tungsten powder or the tungsten compound powder as the tungsten material preferably has a mean particle diameter falling within a range of 0.1 to 100 μm. The mean particle diameter of the tungsten material more preferably falls within a range of 0.3 μm to 10 μm, and still more preferably falls within a range of 0.3 μm to 3 μm, and desirably falls within a range of 0.3 μm to 1.5 μm. When the metal tungsten powder or the tungsten compound powder having the mean particle diameter falling within the above-described range is used, sublimation occurs easily.

When the mean particle diameter of the tungsten material is less than 0.1 μm, the raw material powder is too fine, and thus pre-adjustment of the raw material powder becomes necessary, handleability decreases, and additionally the cost increases, thereby making it unfavorable in an industrial aspect. When the mean particle diameter of the tungsten material exceeds 100 μm, uniform sublimation reaction does not occur easily. Even when the mean particle diameter is large, processing with a large energy amount can cause uniform sublimation reaction, but this is unfavorable in an industrial aspect.

In order to increase antiviral performance, microparticles that have small dispersion in particle diameter and contain a large number of microparticles having a small particle diameter are preferable. In order to obtain such microparticles, it is preferable that a processing amount or an energy application amount is appropriately controlled. Generally, in the case of producing fine and uniform microparticles, a processing amount of microparticle production, heat treatment, or the like is preferably decreased. However, in an industrial aspect, productivity is also needed to be considered, resulting in that a processing amount has to be increased. In the above case, the dispersion in particle diameter or crystallinity of the microparticles is increased easily. However, by optimizing conditions of temperature, time, atmosphere, and so on of the microparticle production and heat treatment, a large number of highly active microparticles are contained, resulting in that the high photocatalytic activity can be exhibited even through dispersions in microparticle property occur.

An example of the method of sublimating the tungsten material in the oxygen atmosphere in the sublimation process is at least one processing selected from inductively coupled plasma processing, arc discharge processing, laser processing, electron beam processing, and gas burner processing. Among them, in the laser processing or the electron beam processing, laser or electron beam is irradiated to perform the sublimation processing. The laser or electron beam has a small irradiation spot diameter, and thus it takes time to process a large amount of raw material at once. However, they have an advantage that it is not necessary to strictly control the particle diameter or stability of supply amount of the raw material powder.

The inductively coupled plasma processing or the arc discharge processing needs adjustment of a generating area of plasma or arc discharge, but it is capable of allowing oxidation reaction of a large amount of raw material powder to occur at once in the oxygen atmosphere. Further, the amount of raw material to be processed at once can be controlled. The gas burner processing needs a relatively low power cost, but it is difficult to process a large amount of raw material powder or raw material solution. Accordingly, the gas burner processing is inferior in productivity. Incidentally, the gas burner processing may be one having sufficient energy for causing sublimation, and is not particularly limited. A propane gas burner, an acetylene gas burner, or the like is used.

In the case when the inductively coupled plasma processing is applied to the sublimation process, generally there is used a method in which plasma is generated using argon gas or oxygen gas, and the metal tungsten powder or the tungsten compound powder is supplied into this plasma. Examples of the method of supplying the tungsten material into the plasma include a method to blow the metal tungsten powder or the tungsten compound powder together with carrier gas, and a method to spray a dispersion liquid in which the metal tungsten powder or the tungsten compound powder is dispersed in a predetermined liquid dispersion medium.

Examples of the carrier gas used when the metal tungsten powder or the tungsten compound powder is blown into the plasma include air, oxygen, and inert gas containing oxygen. Among them, the air is used preferably because of its low cost. When oxygen is contained enough in the reaction field, like in the case where reaction gas containing oxygen is supplied other than the carrier gas, the case where the tungsten compound powder is the tungsten trioxide, or the like, inert gas such as argon or helium may also be used as the carrier gas. For the reaction gas, oxygen, inert gas containing oxygen, or the like is preferably used. In the case of the inert gas containing oxygen being used, the oxygen amount is preferably set so that it is possible to sufficiently supply a necessary oxygen amount for oxidation reaction.

By applying the method of blowing the metal tungsten powder or the tungsten compound powder together with carrier gas, and adjusting the gas flow rate or the pressure or the like in a reaction container, the crystal structure of the tungsten trioxide microparticles can be controlled easily. Concretely, it is easy to obtain tungsten trioxide microparticles having a crystal structure of at least one selected from monoclinic crystal and triclinic crystal (monoclinic crystal, triclinic crystal, or mixed crystal of monoclinic crystal and triclinic crystal) or one in which rhombic crystal is mixed therewith. It is preferable that the crystal structure of the tungsten trioxide microparticles is a mixed crystal of monoclinic crystal and triclinic crystal or a mixed crystal of monoclinic crystal, triclinic crystal, and rhombic crystal.

An example of the dispersion medium used for producing the dispersion liquid of the metal tungsten powder and the tungsten compound powder is a liquid dispersion medium having oxygen atoms in molecules. Using the dispersion liquid facilitates handling of the raw material powder. The liquid dispersion medium having oxygen atoms in molecules includes at least one selected from water and alcohol by 20 capacity % or more. As the alcohol used as the liquid dispersion medium, for example, at least one selected from methanol, ethanol, 1-propanol, and 2-propanol is preferable. Water and alcohol easily evaporate by heat of plasma, so that they do not hinder sublimation reaction or oxidation reaction of the raw material powder, and they easily facilitate oxidation reaction because they contain oxygen in molecules.

When the metal tungsten powder or the tungsten compound powder is dispersed in the dispersion medium to produce the dispersion liquid, the metal tungsten powder or the tungsten compound powder is preferably contained in a range of 10 mass % to 95 mass %, and is more preferably contained in a range of 40 mass % to 80 mass % in the dispersion liquid. By dispersing in the dispersion liquid in such a range, the metal tungsten powder or the tungsten compound powder can be dispersed uniformly in the dispersion liquid. When it is dispersed uniformly, uniform sublimation reaction of the raw material powder occurs easily. When the content in the dispersion liquid is less than 10 mass %, the amount of the raw material powder is too small, and it cannot be produced efficiently. When the content exceeds 95 mass %, the amount of the dispersion liquid is small, the viscosity of the raw material powder increases and makes it sticky to the container, and thus the handleability decreases.

By applying the method to have the metal tungsten powder or the tungsten compound powder in the dispersion liquid and blowing it into plasma, the crystal structure of the tungsten trioxide microparticles can be controlled easily. Concretely, tungsten trioxide microparticles having a crystal structure of at least one selected from monoclinic crystal and triclinic crystal, or one in which rhombic crystal is mixed therewith can be obtained easily. Further, also by using a tungsten compound solution as the raw material, the sublimation reaction can be performed uniformly, and moreover, controllability of the crystal structure of the tungsten trioxide microparticles improves. The method using the dispersion liquid as described above is also applicable in the arc discharge processing.

When the sublimation process is performed by irradiating with laser or electron beam, pelletized metal tungsten or tungsten compound is preferably used as the raw material. The laser or electron beam has a small irradiation spot diameter, and thus supply becomes difficult when the metal tungsten powder or the tungsten compound powder is used. However, using the pelletized metal tungsten or tungsten compound makes it possible to perform sublimation efficiently. The laser may be one having sufficient energy for sublimating the metal tungsten or the tungsten compound and is not particularly limited, but $CO_2$ laser is preferable because of its high energy.

When the pellets are irradiated with the laser or electron beam, moving at least one of the irradiation source of the laser light or electron beam and the pellets enables to effectively sublimate the entire surface of a pellet having a certain degree of size. It is easy to obtain the tungsten trioxide powder having a crystal structure in which rhombic crystal is mixed with at least one selected from monoclinic crystal and triclinic crystal. The pellets as described above are also applicable in the inductively coupled plasma processing and the arc discharge processing.

The tungsten oxide based microparticles used for the antiviral material in this embodiment can be obtained just by the sublimation process as described above, but it is also effective to perform heat treatment process on the tungsten oxide based microparticles produced in the sublimation process. The heat treatment process is to heat treat the tungsten trioxide based microparticles obtained in the sublimation process at predetermined temperatures and for predetermined time in an oxidative atmosphere. Also in the case where the tungsten trioxide microparticles cannot be formed sufficiently by condition control or the like in the sublimation process, the percentage of the tungsten trioxide microparticles in the tungsten oxide microparticles can be 99% or more, substantially 100%, by performing the heat treatment. Moreover, the crystal structure of the tungsten trioxide microparticles can be adjusted to a predetermined structure in the heat treatment process.

Examples of the oxidative atmosphere used in the heat treatment process include air and oxygen-containing gas. The oxygen-containing gas means inert gas containing oxygen. The heat treatment temperature is preferably set to fall within a range of 200 to 1000° C., and more preferably to fall within a range of 400 to 700° C. The heat treatment time is preferably set to fall within a range of 10 minutes to 5 hours, and more preferably to fall within a range of 30 minutes to 2 hours. By having the temperature and time of the heat treatment process in the above-described ranges, the tungsten trioxide can be formed easily from tungsten oxide other than the tungsten trioxide. Further, in order to obtain a powder with less defects and good crystallinity, temperature increase or temperature decrease during heat treatment is preferably performed gradually. Rapid heating or cooling during heat treatment leads to decrease of crystallinity.

When the heat treatment temperature is lower than 200° C., there is a risk that an oxidation effect for turning a powder that did not become the tungsten trioxide in the sublimation process to the tungsten trioxide is not obtained sufficiently. When the heat treatment temperature exceeds 1000° C., the tungsten oxide microparticles grow rapidly, and thus the specific surface area of the obtained fine tungsten oxide powder can decrease easily. Moreover, by performing the heat treatment process at the temperatures and for the time as described above, it becomes possible to adjust the crystal structure and crystallinity of the fine tungsten trioxide powder.

The antiviral material in this embodiment can be applied to various antiviral films, antiviral fibers, and antiviral products. The antiviral material is used by allowing the tungsten oxide based microparticles produced by the production method as described above to adhere to a surface of a base material, or by kneading the tungsten oxide based microparticles into a base material. Examples of a method to allow the tungsten oxide based microparticles to adhere to a surface of a base material include a method to apply a dispersion liquid or coating material in which the tungsten oxide based microparticles are dispersed in a dispersion medium such as water or alcohol to a surface of a base material. By applying such a method, it is possible to obtain an antiviral fiber and an antiviral product each having a film (antiviral film) such as a coated film or coating film containing, the tungsten oxide based microparticles.

The antiviral film preferably contains the antiviral material (tungsten oxide based microparticles) in a range of 0.1 to 90 mass %. When the content of the antiviral material is less than 0.1 mass %, there is a risk that sufficient antiviral performance cannot be obtained. When the content of the antiviral material exceeds 90 mass %, there is a risk that the property as the film deteriorates. The film thickness of the antiviral film preferably falls within a range of 2 to 1000 nm. When the film thickness of the antiviral film is less than 2 nm, an amount of the antiviral material falls short to thereby cause a risk that sufficient antiviral performance cannot be obtained. In the case when the film thickness of the antiviral film exceeds 1000 nm, antiviral performance can be obtained, but the strength as the film, decreases easily. The film thickness of the antiviral film more preferably falls within a range of 2 to 400 nm.

The antiviral film may also contain an inorganic binder and the like besides the antiviral material using the tungsten oxide based microparticles. As the inorganic binder, there is cited an amorphous oxide of at least one element selected from Si, Ti, Al, W, and Zr. The inorganic binder made of the amorphous oxide is used when being added to, for example, a coating material using the tungsten oxide based microparticles as colloidal silica, alumina sol, titania sol, zirconia sol, or the like. The content of the inorganic binder is preferably set to fall within a range of 5 to 95 mass %. When the content of the inorganic binder of the antiviral film exceeds 95 mass %, there is a risk that desired antiviral performance cannot be obtained. When the content of the inorganic binder is less than 5 mass %, there is a risk that sufficient binding strength cannot be obtained.

The antiviral fiber and the antiviral product in this embodiment each include the above-described antiviral material. Concrete forms of the antiviral fiber and the antiviral product include a form in which the antiviral material adheres to a base material or the antiviral material is impregnated into a base material, a form in which a dispersion liquid or coating material containing the antiviral material is applied to a base material, and the like. The antiviral material may also be used by performing processing in which the tungsten based microparticles are mixed, carried, or impregnated with or into a material having adsorption performance such as activated carbon or zeolite. The antiviral film and the antiviral product can be used under irradiation of visible light having illuminance of 1000 lx or less.

The antiviral material, the antiviral film, the antiviral fiber, and the antiviral product are used to be aimed at an antiviral function against at least one virus selected from a low pathogenic avian influenza virus (H9N2), a high pathogenic avian influenza virus (H5N1), and a swine influenza virus. However, they can also be used to be aimed at an antiviral function against a virus other than the above viruses.

Products using the antiviral material, the antiviral film, and the antiviral fiber include products required for an antiviral property, such as air-conditioners, air cleaning devices, electric fans, refrigerators, microwave ovens, dish washer/driers, rice cookers, pots, pot lids, IH heaters, washing machines, vacuum cleaners, lighting apparatuses (lamps, apparatus bodies, shades, and the like), sanitary products, toilets, washbowls, mirrors, bathrooms (walls, ceilings, floors, and the like), building materials (interior walls, ceiling materials, floors, exterior walls, and the like), interior products (curtains, carpets, tables, chairs, sofas, shelves, beds, beddings, and the like), glasses, sashes, hand rails, doors, knobs, clothes, filters used for home electric appliances or the like, stationery, kitchen utensils, medical supplies (white coats, masks, gloves, and the like), medical appliances and devices, and materials used inside automobiles, vehicles of trains, aircrafts, boats and ships, and the like. Examples of a base material include glass, ceramics, plastic, resin such as acryl, paper, fiber, metal, wood, and the like. The antiviral material, the antiviral film, and the antiviral fiber can be applied to a resin or fiber by application, adhesion, and kneading.

The antiviral material, the antiviral film, the antiviral fiber, and the antiviral product in this embodiment each exhibit practical antiviral performance, so that even in the case when they are used under irradiation of visible light having low illuminance such as in ordinary living space or interior space of a vehicle or the like, antiviral performance can be obtained. In interior space of an automobile, for example, antiviral performance can be exhibited even during night with less light. As is an antiviral agent using antiviral metal ions, which has been used conventionally, it is possible to stably exhibit practical antiviral performance without causing deterioration of the performance due to transformation.

Next, concrete examples of the present invention and evaluation results thereof will be described.

EXAMPLE 1

As a raw material, a tungsten oxide pellet having a density of 4.7 g/cm$^3$ was prepared. The pellet was placed in a reaction container and was irradiated with $CO_2$ laser light while supplying oxygen at a flow rate of 10 L/min and maintaining the pressure at 3.5 kPa. Tungsten oxide microparticles are produced by laser processing. The tungsten oxide microparticles were heat treated in the atmosphere under conditions of 900 C.° and 0.5 h, and thereby microparticles in Example 1 were obtained.

The mean primary particle diameter (D50) and the BET specific surface area of the obtained microparticles were measured. The mean primary particle diameter was measured by image analysis of a TEM picture. For TEM observation, H-7100FA made by Hitachi was used, an enlarged picture was subjected to image analysis and 50 microparticles or more were extracted, and integrated diameters with reference to volumes were obtained to calculate the D50. Further, the content ratio was calculated from cumulative frequencies of microparticles having a particle diameter of 40 nm or less. Measurement of the BET specific surface area was performed by using a specific surface area measuring apparatus Macsorb 1201 made by MOUNTECH Co., Ltd. Preprocessing was conducted under conditions of 200° C.×20 minutes in nitrogen. The mean primary particle diameter (D50), the ratio of the microparticles having a particle diameter of 40 nm or less, and the BET specific surface area are shown in Table 1.

Further, the obtained microparticles were subjected to X-ray diffraction. The X-ray diffraction was performed by using an X-ray diffraction instrument RINT-2000 made by Rigaku Corporation and by using a Cu target, a Ni filter, and a graphite (002) monochromator. Measuring conditions were as follows: tube/bulb voltage: 40 kV, tube/bulb current: 40 mA, divergent slit: 1/2°, scattering slit: auto, light-receiving slit: 0.15 mm, 2θ range measured: 20 to 70°, scanning speed: 0.5°/min, and sampling width: 0.004°. In measuring the peak intensities, Kα2 was not removed, and only smoothing and background subtraction processes were performed. The smoothing was conducted by using Savizky-Golay (least-squares method) with a filter point 11. The background subtraction was performed in a manner that a straight line was fit in the measurement range and a threshold value a was set to 3.0. The number of peaks of the microparticles existing in a 22.5 to 25° 2θ range based on the X-ray diffraction result was obtained, and in the case of first, second, and third peaks existing, an intensity ratio of intensity of a valley between the peaks to the first peak was obtained. Results thereof are shown in Table 1.

Next, evaluation of antiviral performance of the obtained microparticles was performed. The microparticles were mixed with water, and then ultrasonic dispersion processing was performed to produce a dispersion liquid. At this time, in order to strengthen adhesion of the microparticles to a specimen base material, colloidal silica of 0.1 in mass % with respect to the microparticles was mixed with the dispersion liquid. The above dispersion liquid was spread on a glass plate of 5×5 cm and dried at 200 C.° for 30 minutes to thereby produce a sample having the tungsten oxide microparticles of 10 mg applied thereon. An adhesion amount of the microparticles is 0.4 mg/cm$^2$. Here, as an unprocessed specimen, a glass plate having colloidal silica in an amount the same as that of the sample only applied thereto was produced.

The antiviral property evaluation of the specimens was performed based on "Test method for antibacterial activity of photocatalytic products under photoirradiation and efficacy" of JIS-R-1702 (2006). A white fluorescent light (FL20SS·W/18, made by Toshiba Lighting & Technology Corporation) was used as a light source, and an ultraviolet cutting filter (Kralex N-169, made by Nitto Jushi Kogyo Co., Ltd.) was used to cut wavelengths under 380 nm, and illuminance was adjusted to 6000 lx. In place of bacteria, a low pathogenic avian influenza virus (subtype H9N2) was used to measure a virus titer (virus infectivity).

Concrete evaluation steps are as follows. First, 100 μL of the influenza virus was inoculated on each of the specimen and unprocessed specimen to be evaluated, and each of surfaces was covered with a film, and the specimen and the unprocessed specimen still stood under conditions of 35±1 C.° and relative humidity of 90%. Next, the specimen and the unprocessed specimen were irradiated with visible light having illuminance of 6000 lx from the fluorescent light, and after a fixed reaction time (0 h and 24 h) lapsed, each virus solution was diluted with a physiological saline solution to be collected. Further, each collected liquid was gradually diluted ten times and was allowed to infect cultured MDCK cells (Madin-Darby canine kidney cells) to be cultured for five days at 37° C. at a $CO_2$ concentration of 5%. After the culturing, the presence or absence of cell morphological transformation (a cytopathic effect) was observed and an amount of the virus that has infected the 50% cultured cell was calculated, and thereby a virus titer per 1 mL (TCID50/mL) was obtained.

An evaluation test of the virus titer was performed three times and a mean value of the virus titers was obtained. Further, the virus titer of the specimen (specimen having the microparticles adhere thereto) obtained after the 24-hour irradiation of visible light having illuminance of 6000 lx was subtracted from the virus titer of the unprocessed specimen obtained after the 24-hour irradiation of visible light having illuminance of 6000 lx, and thereby the inactivation effect R [6000 lx, 24 h] was obtained. Similarly, the inactivation effect R [1000 lx, 24 h] was obtained from the virus titers each obtained after 24-hour irradiation of visible light having illuminance of 1000 lx, and the inactivation effect R [6000 lx, 4 h] was obtained from the virus titers each obtained after 4-hour irradiation of visible light having illuminance of 6000 lx. Results thereof are shown in Table 1.

In the unprocessed specimen, a logarithmic value (logTCID50) of the virus titer decreased by about one between before the visible light irradiation and after the 24-hour irradiation of visible light having illuminance of 6000 lx. It is said that the above decrease simply falls within a decrease range equivalent to that of the case when only a glass plate is employed and no light irradiation is performed, and falls within a natural decrease range. The tungsten oxide microparticles in Example 1 exhibited antiviral performance but the value of the inactivation effect R was small because the particle diameter was slightly large. The inactivation effect R in the case of the 4-hour irradiation of visible light having illuminance of 6000 lx was equal to or less than one, and the effect was smaller. These results are conceivably because the particle diameter of the tungsten oxide microparticles was slightly large to thereby make the tungsten oxide microparticles difficult to come into contact with the virus, and decomposition of proteins by a photocatalytic effect did not go easily.

EXAMPLE 2

A tungsten trioxide powder having a mean particle diameter of 0.5 μm was prepared as a raw material powder. This raw material powder was sprayed with carrier gas (Ar) on RF plasma, and further, as reaction gas, oxygen was supplied at a flow rate of 80 L/min. At this time, the pressure in a reaction container was adjusted to 20 kPa. In this manner, the sublimation process of subjecting the raw material powder to oxidation reaction while sublimating it was performed to produce tungsten oxide microparticles. Powder properties of the mean particle diameter (D80) of the obtained tungsten oxide microparticles, the ratio of microparticles having a particle diameter of 40 nm or less, the BET specific surface area, and the like were measured similarly to Example 1. Further, X-ray diffraction evaluations of the number of peaks of the microparticles existing in a 22.5 to 25° 2θ range based on the X-ray diffraction result, and in the case of first, second, and third peaks existing, an intensity ratio of intensity of a valley between the peaks to the first peak, and the like were performed similarly to Example 1. Results thereof are shown in Table 1.

Similarly to Example 1, the tungsten oxide microparticles were applied on a glass plate to produce a specimen, and a virus titer obtained after 24-hour irradiation of visible light having illuminance of 6000 lx, a virus titer obtained after 24-hour irradiation of visible light having illuminance of 1000 lx, and a virus titer obtained after 4-hour irradiation of visible light having illuminance of 6000 lx were evaluated respectively, and each of the inactivation effects R was obtained. Results thereof are shown in Table 1. The microparticles in Example 2 exhibited the high inactivation effect in all the cases.

EXAMPLES 3 to 5

Tungsten oxide microparticles were produced by performing the sublimation process similarly to Example 2 except that argon gas was supplied at a flow rate of 40 L/min, and air was supplied at a flow rate of 40 L/min as reaction gas, and the pressure in a reaction container was adjusted to 40 kPa. However, only in Example 5, a raw material application speed was set to be 1.4 times faster than that of Example 2 and other conditions. Further, in Example 3, the obtained microparticles were heat treated under conditions of 550 C.° and 1 h, in Example 4, the obtained microparticles were heat treated under conditions of 750 C.° and 1 h, and in Example 5, the obtained microparticles were heat treated under conditions of 800 C.° and 0.25 h. Powder properties of the microparticles in Examples 3 to 5 obtained in this manner and results of the X-ray diffraction evaluations are shown in Table 1. Further, with respect to the obtained microparticles, virus titers were evaluated to obtain the inactivation effects R similarly to Example 1. Results thereof are shown in Table 1.

In Examples 3 to 5, the high inactivation effect was exhibited in all the cases, and the microparticles containing microparticles having a smaller particle diameter exhibited a higher effect. Further, in the case when the mean primary particle diameters were substantially the same, the microparticles containing a large number of small microparticles having a particle diameter of 40 nm or less exhibited the higher inactivation effect. This is conceivably because the particle diameter was sufficiently small with respect to the size of the virus, and further the microparticles containing a large number of smaller microparticles had a large contact area, and thus the inactivation effect was increased. The reason why even though the particle diameter in Example 3 was larger than that in Example 2, the microparticles in Example 3 exhibited high antiviral performance is conceivably because crystallinity of the tungsten oxide microparticles improved, and the tungsten oxide microparticles had less defects or the like, and thus photocatalytic performance by an organic matter decomposition property improved.

EXAMPLES 6 TO 13

In Example 6, the sublimation process and heat treatment process similar to those in Example 3 except that a tungsten oxide powder with a large amount of impurities such as Fe and Mo is used as a raw material to be placed in plasma were performed to produce tungsten oxide composite microparticles containing 500 ppm of Fe. In Example 7, a copper oxide (CuO) powder of 0.5 mass % was mixed with the tungsten oxide microparticles obtained in Example 3 to produce composite microparticles. In Example 8, a titanium oxide powder was mixed with the tungsten oxide microparticles obtained in Example 3 by a ratio of 10 mass % to produce composite microparticles.

In Example 9, the sublimation process and heat treatment process similar to those in Example 3 except that a zirconium oxide powder is mixed with a tungsten oxide powder to be used as a raw material to be placed in plasma were performed to produce tungsten oxide composite microparticles containing 0.2 mass % of zirconium (Zr). In Example 10, the tungsten oxide microparticles obtained in Example 3 were dispersed in an aqueous palladium chloride solution. This dispersion liquid was centrifugally separated, cleaning by removal of a supernatant liquid and addition of water was performed twice, and thereafter the powder from which the supernatant liquid was removed was dried at 110° C. for 12 hours to thereby produce tungsten oxide composite microparticles containing 0.5 mass % of palladium (Pd).

In Example 11, the tungsten oxide microparticles obtained in Example 3 were dispersed in an aqueous manganese chloride solution. This dispersion liquid was centrifugally separated, cleaning by removal of a supernatant liquid and addition of water was performed twice or more, and thereafter the microparticles from which the supernatant liquid was removed were dried at 110° C. for 12 hours to thereby produce tungsten oxide composite microparticles containing 0.05 mass % of manganese (Mn).

In Example 12, the tungsten oxide microparticles obtained in Example 3 were dispersed in an aqueous chloroplatinic acid solution, visible light irradiation was performed and methanol was put in, and carrying by a photoprecipitation method was performed. Centrifugal separation was conducted, cleaning by removal of a supernatant liquid and addition of water was performed twice, and thereafter the powder from which the supernatant liquid was removed was dried at 110° C. for 12 hours to thereby produce tungsten oxide composite microparticles containing 0.2 mass % of platinum (Pt).

In Example 13, the tungsten oxide microparticles obtained in Example 3 were dispersed in an aqueous silver nitrate solution, and carrying by photoreduction processing was performed. Centrifugal separation was conducted, cleaning by removal of a supernatant liquid and addition of water was performed twice, and thereafter the powder from which the supernatant liquid was removed was dried at 110° C. for 12 hours to thereby produce tungsten oxide composite microparticles containing 0.01 mass % of silver (Ag).

Powder properties of the microparticles obtained as above and results of the X-ray diffraction evaluations are shown in Table 1. Further, virus titers of the obtained microparticles were evaluated similarly to Example 1 to obtain the inactivation effects R. Results thereof are shown in Table 1. The composite microparticles obtained in Examples 6 to 13 each exhibited the inactivation effect R being equal to or better than that of Example 3 and had a high antiviral property.

EXAMPLES 14 AND 15

In Example 14, the tungsten oxide microparticles obtained in Example 3 were dispersed in an alumina sol, and this dispersion liquid was dried at 110° C. for 12 hours to thereby produce tungsten oxide composite microparticles containing 2 mass % of alumina ($Al_2O_3$). In Example 15, the tungsten oxide microparticles obtained in Example 3 were dispersed in an aqueous cerium chloride solution. This dispersion liquid was centrifugally separated, cleaning by removal of a supernatant liquid and addition of water was performed twice, and thereafter the powder from which the supernatant liquid was removed was dried at 110° C. for 12 hours to thereby produce tungsten oxide composite microparticles containing 0.1 mass % of Ce. Properties of these microparticles are shown in Table 1.

COMPARATIVE EXAMPLE 1

The same measurement and evaluation as those of Example 1 were performed by using a tungsten oxide powder (made by Rare Metallic Co., Ltd.) available on the market as a reagent. Powder properties are shown in Table 1. Further, similarly to Example 1, tungsten oxide microparticles were applied on a glass plate, but it was not possible to form a film because the particle diameter of the tungsten oxide based microparticles was noticeably large, resulting in that it was not possible to evaluate virus titers.

COMPARATIVE EXAMPLE 2

A nitrogen doped titanium oxide powder as a visible light response-type photocatalyst was used to evaluate virus titers similarly to Example 1. Powder properties and the inactivation effect are shown in Table 1. It was hardly possible for the nitrogen doped titanium oxide powder to obtain antiviral performance under irradiation of light having low illuminance for a short period of time because the inactivation effect obtained after 24-hour irradiation of visible light having illuminance of 6000 lx was 0.1, which was small.

COMPARATIVE EXAMPLE 3

Alcohol generally used for sterilization and a virus were inoculated on a glass plate of 5×5 cm simultaneously to evaluate virus titers. Results thereof are shown in Table 1. The inactivation effect against the virus was obtained. However, in the case when the glass plate used for the test was used for the evaluation again, no inactivation effect was obtained, resulting in that it is of course that there was no effect after volatilization of the alcohol.

EXAMPLES 16 AND 17

In Example 16, 5 mass % of the tungsten oxide microparticles obtained in Example 3 was mixed with 0.5 mass % of amorphous $ZrO_2$ and water and dispersed to adjust an aqueous coating material. This aqueous coating material was applied to a ceramic plate to form a tungsten oxide composite film. The film thickness is about 200 nm. A specimen of 5×5 cm was cut out of a member including such a microparticle film, and an antiviral property of the film was evaluated in a manner similar to that of the evaluation of the microparticles. Note that an unprocessed ceramic plate was used as an unprocessed specimen at this time.

In Example 17, the tungsten oxide microparticles obtained in Example 3 were dispersed in water to adjust a water dispersion liquid, and the water dispersion liquid was applied to a cotton fiber cloth with weight of 90 g/m² with a $SiO_2$ binder. An applied amount of microparticles was 0.4 mg/cm². A specimen of 5×5 cm was cut out of such a fiber cloth having the microparticles applied thereto, and an antiviral property of the microparticles was evaluated in a manner similar to that of the microparticles. Note that as an unprocessed specimen at this time, a cloth to which a $SiO_2$ binder in an amount the same as that of a sample was only applied was used.

There are shown powder properties of the microparticles used in Example 16 and Example 17 and results of the X-ray diffraction evaluations in Table 1. Similarly to Example 1, virus titers of the film and the fiber were evaluated to obtain the inactivation effects R. Results thereof are shown in Table 1. In both Example 16 and Example 17, the inactivation effect R was high, which was similar to the evaluation of the microparticles, and even though the film was formed of the tungsten oxide microparticles, and further the tungsten oxide microparticles were applied to the fiber, the film and fiber each had a high antiviral property.

EXAMPLE 18

In order to evaluate the durability of antiviral performance, the virus titer of a member in Example 14 was evaluated immediately after a film was formed and after the film was maintained for six months under a general environment. The inactivation effect R [6000 lx, 24 h] was 4.5 and 4.4, and it was confirmed that a high antiviral property is maintained even after the 6-month maintenance.

COMPARATIVE EXAMPLE 4

An Ag-based antibacterial agent was applied to a glass plate of 5×5 cm to evaluate its virus titers. Results thereof are shown in Table 1. The Ag-based antibacterial agent exhibited a high antiviral property. However, the Ag-based antibacterial agent is expensive and furthermore has a possibility to cause a metal allergy. Further, as a result of the evaluation of the virus titer after the glass plate having the Ag-based antibacterial agent applied thereto was left to stand for six months, the inactivation effect almost disappeared. It was confirmed that the antibacterial agent has a short performance duration.

film thickness of a film formed at this time was about 50 nm. As a result of the evaluation, the inactivation effect R obtained after 24-hour irradiation of visible light having illuminance of 6000 lx was 1.5, and the value decreased because of a decrease in the adhesion amount, but it was confirmed that Example 16 has an antiviral property. It is conceivable that the particle diameter of a tungsten oxide powder was small, thereby allowing a uniform coating layer to be formed, so that a high antiviral property was obtained even with a small amount of the powder.

As above, it is found that the antiviral material using the tungsten oxide microparticles or the tungsten oxide composite microparticles, and further the antiviral film, the antiviral fiber, and the antiviral product each using the antiviral material can all exhibit practical antiviral performance for a long period of time. Further, they each exhibit a high antiviral property even under visible light having low illuminance.

Further, it was confirmed that when the tungsten oxide microparticles or the tungsten oxide composite microparticles are contained in zeolite, activated carbon, porous ceramic, diatomite, and the like, and they are used for filters and building materials, it is possible to decrease not only viruses in living space but also occurrences of bacteria and molds. Accordingly, by employing such an antiviral material, it becomes possible to provide a film, fiber, and product each exhibiting practical antiviral performance for a long period of time.

TABLE 1

| | POWDER PROPERTIES | | | | ANTIVIRAL TEST RESULTS | | |
|---|---|---|---|---|---|---|---|
| | MEAN PRIMARY PARTICLE DIAMETER (D50) [nm] | BET SPECIFIC SURFACE AREA [m²/g] | RATIO Or PARTICLES Or 40 nm OR LESS [%] | XRD PEAK NUMBER | XRD PEAK VALLEY INTENSITY RATIO [%] | INACTIVATION EFFECT R [6000lx, 24 h] | INACTIVATION EFFECT R [1000lx, 24 h] | INACTIVATION EFFECT R [6000lx, 4 h] |
| EXAMPLE 1 | 110 | 7.8 | 3 | 3 | 8 | 1.9 | 1.1 | 0.4 |
| EXAMPLE 2 | 3 | 257 | 100 | 2 | — | 4.2 | 3.1 | 1.1 |
| EXAMPLE 3 | 23 | 34 | 80 | 3 | 45 | 4.6 | 3.8 | 1.5 |
| EXAMPLE 4 | 75 | 11 | 5 | 3 | 10 | 3.5 | 2.6 | 0.7 |
| EXAMPLE 5 | 79 | 11 | 20 | 3 | 25 | 3.9 | 3.0 | 1.0 |
| EXAMPLE 6 | 22 | 36 | 80 | 3 | 40 | 4.5 | 3.9 | 1.5 |
| EXAMPLE 7 | 27 | 29 | 80 | 3 | 40 | 4.7 | 4.0 | 1.7 |
| EXAMPLE 8 | 24 | 33 | 80 | 3 | 40 | 4.4 | 3.8 | 1.5 |
| EXAMPLE 9 | 25 | 32 | 80 | 3 | 40 | 4.4 | 3.8 | 1.6 |
| EXAMPLE 10 | 23 | 34 | 80 | 3 | 40 | 4.6 | 4.0 | 2.0 |
| EXAMPLE 11 | 22 | 36 | 80 | 3 | 40 | 4.4 | 3.0 | 1.5 |
| EXAMPLE 12 | 27 | 30 | 80 | 3 | 40 | 4.7 | 3.9 | 2.2 |
| EXAMPLE 13 | 25 | 32 | 80 | 3 | 40 | 4.7 | 4.0 | 2.4 |
| EXAMPLE 14 | 23 | 34 | 80 | 3 | 40 | 4.5 | 3.7 | 1.4 |
| EXAMPLE 15 | 23 | 33 | 80 | 3 | 40 | 4.5 | 3.8 | 1.5 |
| EXAMPLE 16 | 23 | 34 | 80 | 3 | 40 | 4.5 | 3.8 | 1.6 |
| EXAMPLE 17 | 23 | 33 | 80 | 3 | 40 | 4.4 | 3.7 | 1.6 |
| COMPARATIVE EXAMPLE 1 | 1200 | 0.7 | 1 | 3 | 3 | x | x | x |
| COMPARATIVE EXAMPLE 2 | 10 | 136 | 90 | — | — | 0.1 | 0 | 0 |
| COMPARATIVE EXAMPLE 3 | — | — | — | — | — | 3.3 | 3.5 | 3.5 |
| COMPARATIVE EXAMPLE 4 | — | — | — | — | — | 3.8 | 3.5 | 3.2 |

EXAMPLE 19

Virus titers were evaluated in a manner similar to that in Example 3 except that 2.5 mg of the tungsten oxide microparticles obtained in Example 3 was applied to a glass plate of 5×5 cm to produce a specimen. An adhesion amount of the tungsten oxide microparticles was 0.1 mg/cm² and the Further, the tungsten oxide microparticles or the tungsten oxide composite microparticles are used to produce an aqueous dispersion liquid, and the aqueous dispersion liquid is applied to a mask or a white coat with a binder, and thereby it is possible to suppress viruses and bacteria that cause nosocomial infection without deteriorating a fiber to be a base material. Further, it is also possible to obtain decomposing performance for organic gas such as acetaldehyde. Besides, the aqueous dispersion liquid can be used suitably also for members used in the interior space of an automobile, building materials and interior materials used in factories, shops, schools, public facilities, hospitals, welfare facilities, accommodations, houses, and the like, and home electronic appliances, cloths, medical supplies, and the like.

Incidentally, while certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and sprit of the inventions.

What is claimed is:

1. An antiviral film, comprising:
tungsten oxide microparticles having a mean primary particle diameter (D50) in a range of 5.5 to 75 nm, the mean primary particle diameter (D50) being a D50 diameter of integrated diameter with reference of volumes of 50 pieces or more of microparticles extracted from an image analysis of a SEM or TEM photograph of the microparticles; and
an inorganic binder for binding the tungsten oxide microparticles, a content of the inorganic binder in the antiviral film being from 5 to 95 mass %, and the inorganic binder being made only of an amorphous metal oxide,
wherein in a X-ray diffraction chart when the tungsten oxide microparticles are measured by X-ray diffractometry, an intensity ratio of a peak A to a peak D (A/D) and an intensity ratio of a peak B to the peak D (B/D) are in a range of 0.7 to 2.0, and an intensity ratio of a peak C to the peak D (C/D) is in a range of 0.5 to 2.5, wherein the peak A is a peak existing in 2θ range from 22.8 to 23.4°, the peak B is a peak existing in 2θ range from 23.4 to 23.8°, the peak C is a peak existing in 2θ range from 24.0 to 24.25°, and the peak D is a peak existing in 26 range from 24.25 to 24.5°,
wherein the tungsten oxide microparticles contain 15% or more of microparticles having a primary particle diameter of 40 nm or less,
wherein a thickness of the antiviral film is in a range of from 2 to 400 nm, and
wherein the tungsten oxide microparticles have an inactivation effect R of 2 or more, as expressed by following:

$$R = \log C - \log A$$

wherein C denotes a virus titer tissue culture infective dose (TCID50) obtained after irradiating an unprocessed specimen with visible light for 24 hours, and A denotes a virus titer TCID50 obtained when the specimen is tested in the following manner:
a) said microparticles are adhered to a specimen in a range of 0.01 mg/cm$^2$ to 40 mg/cm$^2$;
b) the specimen from step (a) is inoculated by a virus titer, wherein said virus is selected from a pathogenic avian influenza virus H9N2, H5N1, and a swine influenza virus;
c) said inoculated specimen from step (b) is irradiated with visible light having a wavelength of 380 nm or more and an illuminance of 6000 lx for 24 hours using a white fluorescent lamp and an ultraviolet cutting filter, and then evaluated for antibacterial activity of photocatalytic products under photoirradiation by Test method JIS-R-1702 (2006).

2. The antiviral film according to claim 1, wherein the amorphous metal oxide contains at least one element selected from the group consisting of silicon, titanium, aluminum, tungsten, and zirconium.

3. The antiviral film according to claim 1, wherein the tungsten oxide microparticles have a BET specific surface area in a range of 16 to 300 m$^2$/g.

4. The antiviral film according to claim 1, wherein the tungsten oxide microparticles have at least one crystal structure selected from a monoclinic crystal of tungsten trioxide and a triclinic crystal of tungsten trioxide, or a crystal structure in which a rhombic crystal of tungsten trioxide is mixed with at least one selected from the monoclinic crystal and the triclinic crystal.

5. An antiviral product, comprising:
a substrate; and
the antiviral film according to claim 1, provided on the substrate.

6. The antiviral film according to claim 1, wherein the tungsten oxide microparticles have a mean primary particle diameter (D50) in a range of 5.5 to 51 nm.

7. The antiviral film according to claim 1, wherein the tungsten oxide microparticles contain 80% or more of the microparticles having the primary particle diameter of 40 nm or less.

8. The antiviral film according to claim 1, wherein the tungsten oxide microparticles are included in a range of 0.01 mg/cm$^2$ to 40 mg/cm$^2$ in the antiviral film.

9. The antiviral film according to claim 1, wherein the tungsten oxide microparticles have a crystal structure in which a rhombic crystal of tungsten trioxide is mixed with at least one selected from a monoclinic crystal of tungsten trioxide and a triclinic crystal of tungsten trioxide.

10. The antiviral film according to claim 1, wherein the tungsten oxide microparticles have a crystal structure in which a rhombic crystal of tungsten trioxide is mixed with a monoclinic crystal of tungsten trioxide and a triclinic crystal of tungsten trioxide.

11. The antiviral film according to claim 1, wherein the amorphous metal oxide contains at least one element selected from the group consisting of titanium, aluminum, tungsten, and zirconium.

12. The antiviral film according to claim 1, wherein the inorganic binder is made only of at least one selected from the group consisting of colloidal silica, alumina sol, titania sol, and zirconia sol.

13. The antiviral film according to claim 1, wherein the inorganic binder is made of at least one selected from the group consisting of alumina sol, titania sol, and zirconia sol.

* * * * *